United States Patent [19]
Motta

[11] Patent Number: 5,662,935
[45] Date of Patent: Sep. 2, 1997

[54] PROCESS FOR PREPARING CONTROLLED RELEASE PHARMACEUTICAL FORMS AND THE FORMS THUS OBTAINED

[75] Inventor: Giuseppe Motta, Bologna, Italy

[73] Assignee: Saitec S.R.L., Castel Guelfo de Bologna, Italy

[21] Appl. No.: 464,708

[22] PCT Filed: Dec. 23, 1993

[86] PCT No.: PCT/IT93/00136

§ 371 Date: Jun. 23, 1995

§ 102(e) Date: Jun. 23, 1995

[87] PCT Pub. No.: WO94/14421

PCT Pub. Date: Jul. 7, 1994

[30] Foreign Application Priority Data

| Dec. 23, 1992 | [IT] | Italy | B092A0455 |
| Jun. 24, 1993 | [IT] | Italy | B093A0294 |
| Nov. 12, 1993 | [IT] | Italy | B093A0460 |

[51] Int. Cl.⁶ .................... A61K 9/14; A61K 9/22; A61K 9/24; A61K 9/26; A61K 9/52
[52] U.S. Cl. .................. 424/465; 424/424; 424/425; 424/443; 424/456; 424/457; 424/458; 424/464; 424/468; 424/469; 424/472; 424/484; 424/485; 424/486; 424/487; 424/488; 424/489; 514/770; 514/772.2; 514/772.3; 514/772.6; 514/774; 514/777; 514/781; 514/776; 514/782; 514/784; 514/951; 514/953
[58] Field of Search .................... 424/464, 465, 424/489, 486, 487, 488, 484, 485, 452, 425, 443, 456

[56] References Cited

U.S. PATENT DOCUMENTS

| 2,828,206 | 3/1958 | Rosenberg | 99/2 |
| 3,078,216 | 2/1963 | Greif | 167/82 |
| 3,137,630 | 6/1964 | Hecker et al. | 167/81 |

(List continued on next page.)

FOREIGN PATENT DOCUMENTS

| 15381 | 9/1980 | European Pat. Off. . | |
| 80341 | 6/1983 | European Pat. Off. . | |
| 0 123 470 | 10/1984 | European Pat. Off. | A61K 31/135 |
| 392608 | 10/1990 | European Pat. Off. . | |
| 1044572 | 10/1966 | United Kingdom | A61K 3/76 |
| 92 5774 | 4/1992 | WIPO . | |

OTHER PUBLICATIONS

Patent Abstract of Japan, JP 3287544, Dec. 18, 1991, vol. 16, No., 114, Mar. 23, 1992, see abstract.
DATABASE WPI, Section Ch. Week 7243, Derwent Purblications Ltd., Class A03, AN 72-69291T & JP,A,47 020 327 Mar. 4, 1971.
DATABASE WPI, Section Ch, Week 8346, Derwent Publications Ltd., Class B04, An 83-818128 & JP,A,58 172 311 Apr. 2, 1982.
DATABASE WPI, Section Ch, Week 8908, Derwent Publications Ltd., Class A03, AN 89-057693 & JP,A,1 009 932 Jul. 1, 1987.
DATABASE WPI, Section Ch, Week 88527, Derwent Publications Ltd., Class A03, AN 85-162944 & JP,A,60 094 403 Oct. 27, 1983.

*Primary Examiner*—Thurman K. Page
*Assistant Examiner*—James M. Spear
*Attorney, Agent, or Firm*—Cushman Darby & Cushman Intellectual Property Group of Pillsbury Madison & Sutro LLP

[57] ABSTRACT

An improved process for preparing controlled release pharmaceutical forms comprises exposing a mixture comprising one or more excipients and one or more active ingredients compatible with each other and with said excipients to mechanical or electromechanical actions for a well established time and within a wide range of frequencies to give tablets, matrices or mono or multilayered films. Said forms can be optionally crushed to give a granulate or powder. Depending on the employed excipient, a delayed or rapid but always controllable release of the active ingredient can be attained.

20 Claims, 6 Drawing Sheets

U.S. PATENT DOCUMENTS

| | | | |
|---|---|---|---|
| 3,146,167 | 8/1964 | Lantz et al. | 167/82 |
| 3,432,593 | 3/1969 | Shepard | 424/20 |
| 3,492,397 | 1/1970 | Peters et al. | 424/20 |
| 3,922,339 | 11/1975 | Shear | 424/19.22 |
| 4,341,759 | 7/1982 | Bogentoft et al. | 424/21 |
| 4,572,833 | 2/1986 | Pedersen et al. | 424/20 |
| 4,657,543 | 4/1987 | Langer et al. | 604/891 |
| 4,779,806 | 10/1988 | Langer et al. | 604/891 |
| 5,306,505 | 4/1994 | Kuzuya et al. | 424/464 |

PROCESS FOR PREPARING CONTROLLED RELEASE PHARMACEUTICAL FORMS AND THE FORMS THUS OBTAINED

This application is a 371 of PCT/IT93/00136 filed Dec. 23, 1993.

TECHNICAL FIELD

The present invention relates to an improved process for preparing pharmaceutical forms with controlled release of the active ingredient and the forms thus obtained. More particularly, it relates to a process for preparing pharmaceutical forms with delayed or rapid release of the active ingredient, said delayed or rapid release being achieved by selecting appropriate excipient(s) to be mixed with the drug(s) and subjecting the mixture thus obtained to mechanical or electromechanical actions for a well established time and within a wide range of frequencies. The present invention elates also to the forms thus obtained, which can be administered by oral, topic or parenteral route, and which can be used also in veterinary field or, when for releasing vegetal hormones, pesticides, fragrances, preservants, also in agroindustrial field.

BACKGROUND ART

The controlled release of an active ingredient from a pharmaceutical form containing it, is well known in the art. Generally, said systems contain one or more excipients which modulate the release acting as disgregating agents or as solubilizers, wetting agents etc., and/or one or more polymeric materials acting as excipients or barriers limitating the release and capable to control the release rate of the therapeutic agent. Said excipients should be logically compatible with the active ingredients and the administration site, stable in the action site, capable to interact with the active ingredient and the biologic fluids so as to provide the desired release control. They should be also easy available and not expensive. It is thus evident that the search for excipients always more sophisticated and adaptable to the different requirements is not presently ended. This is due both to the diversity and sometime complexity of the drugs to be used, and to the desire to obtain pharmaceutical forms even more sophisticated and reliable.

Thus in U.S. Pat. No. 2,828,206 discrete, free flowing particles are described, each comprising at least one inner core of fat-soluble vitamin material, said core being coated with a shell of a fat-insoluble substance selected from the group consisting of protein, gums, carbohydrates and pectin, which is in turn coated with a member of the group consisting of fats and waxes having a melting point between 45° and 95° C.

GB-A-1,044,572 claims a pharmaceutical composition providing prolonged release of a drug in the gastro-intestinal tract comprising a multitude of medicinal pellets randomly coated with a fatty acid coating comprising a saturated fatty acid or mixture of saturated fatty acids having from 12 to 22 carbon atoms per molecule, said coating being modified by an inert dusting powder which serves to form channels or pores through the otherwise continuous coating.

In U.S. Pat. No. 4,341,759 granules containing a pharmaceutically active material and at least one pharmaceutically inactive release controlling component are described, wherein said granules have a core and an outer layer comprising at least one active compound and at least one inactive release controlling substance over a period of time sufficient to cause said unitary layer to form on each core to give granules of size 0.3–2 mm.

U.S. Pat. No. 4,572,833 relates to a method for preparing a pharmaceutical oral controlled release composition, in which individual units comprise units of an active substance which is subject to controlled release as a result of coating the units with a substantially water—insoluble but water-diffusable controlled release coating comprising applying, on units comprising the active substance, a film-coating mixture comprising a solvent, a film-forming substance dissolved in the solvent and a hydrophobic substance substantially micro-dispersed in the film-coating mixture in a molten, but undissolved state, the film-coating mixture being applied at a temperature above the melting point of the hydrophobic substance.

U.S. Pat. No. 3,078,216 describes an oral pharmaceutical preparation having a prolonged release comprising a plurality of medicament granules, substantially all being from 12 mesh to 80 mesh, each coated with a layer of water insoluble, partly digestible hydrophobic material, the thickness of coating varying directly with particle size whereby in oral use the very fine granules rapidly release their medicament and the granules of increasing size release their medicament more and more slowly.

In U.S. Pat. No. 3,922,339 a process of preparing a sustained release pharmaceutical preparation of a medicament is described, which comprises (1) blending a medicament with desired inert materials, (2) wetting the blend with sufficient liquid material so as to act as a binder on compacting, (3) compacting the wetted blend by extruding to form a spaghetti-like material, (4) drying, breaking and screening the extruded material to the desired particle size, (5) spraying the particles with a solution of a film-forming material, (6) dusting the sprayed particles with a powder and drying to form a seal on the particles, and (7) coating the sealed particles with a solution of an excipient so as to form an enteric-soluble coating on the sealed particle.

From U.S. Pat. No. 3,432,593 a granule, capsule or tablet is known, having the active medicament adsorbed on a complex colloidal magnesium aluminum silicate. The individual granules may be further provided with one or more suitable retardant coatings, each of which provides a predetermined period of sustainment.

Further details concerning the preparation of pharmaceutical forms with controlled release of the active substance are reported for example in U.S. Pat. Nos. 3,137,630 and 8,492,397 as well as in EP-A-123,470.

From what stated above, it is clear that the controlled release technique has been widely used and studied, but the attempts to effect new improvements thereon go on unceasingly. Generally, the methods utilized for having suitable matrices inglobating the active ingredient are: compaction with pressure, granulation, extrusion and the film-forming procedure.

However, each of the above mentioned methods has many disadvantages. So dry compaction is possible only with suitable materials, requires the use of specific excipients which not always are compatible with the possible therapeutic uses, and is quite complex, requiring rather expensive apparatus. The wet granulation exposes the drug and the excipients to the deleterious water and heat action, is long and expensive and normally requires the use of binders that could interfere with the biodisponibility of the drug.

Also the film-forming procedure exposes the active ingredient and the excipients to the deleterious action of heat, water or other solvents; it needs long time and is expensive. Extrusion is then possible only with materials able to assume a plastic consistency with heat and submits thus the active ingredient and the excipient to a prolonged and potentially deleterious heating.

There at least to note that in the controlled release pharmaceutical forms the release kinetic is not always optimal. Often said release is in fact too slow or too rapid, that is not controlled. Said dosage forms are thus not free from problems, in that the need a high administration rate and can cause high fluctuations of drug in ematic and tissue concentrations and toxic effects arising from overdosage, with onset of the risk of severe side effects. In other cases a deficient therapeutic efficacy can be observed, arising from an insultable release kinetic or from a low user's compliance, that is from the non-taking of the drug when said taking is too frequent, unpleasant for the patient or causes negative side effects due to high peaks of ematic concentration of the drug.

Attempts have been made to solve at last partly all these problems employing ultrasonic energy. Thus in EP-A-0 467 743 a process for compacting a powder mixture is described, in which a non-thermoplastic product is blended with a thermoplastic one and the mixture thus obtained is submitted to ultrasonic energy with pressure. An adsorbing tablet is thus formed that can be imbued with a perfume and applied on the skin, or an adsorbing strip which can be imbued with a drug.

In U.S. Pat. No. 4,657,543 a process for delivering a biologically active substance on a demand is described, said process comprising the steps of combining a biologically active substance with a biocompatible polymeric composition as an admixture, forming said admixture into a shaped, solid polymeric matrix, implanting said solid polymeric matrix in vivo at a preselected site such that said solid implanted matrix is in a liquid environment, and exposing said implanted solid polymeric matrix to ultrasonic energy for a predetermined time to effect cavitation of said solid polymeric matrix by rapid compression with subsequent expansion of liquid or solid surrounding said solid polymeric matrix thereby to control the rate of release of said biologically active substance from said matrix over a specific time period wherein the rate of release is changed during said time period.

From U.S. Pat. No. 4,779,806 a process for delivering a composition on demand is at last known, which comprises incorporating said composition within a polymeric matrix, surrounding said composition and polymeric matrix with a liquid medium, and exposing said polymeric matrix to ultrasonic energy for a predetermined time and at a frequency to effect cavitation of said polymeric matrix to release said composition from said matrix in a controlled manner over a specific time period.

In all the literature mentioned above, with controlled release of a drug almost always a delayed release is meant, that is a release that permits the drug to be released slowly to the body. In both the last mentioned US patents use was then made ultrasonic energy for having cavitation of a polymeric matrix, but also in this case a delayed release is achieved and it is necessary to implant a matrix in vivo and to degrade the matrix for having the desired release. It is also known that cavitation exhibits a few disadvantages, the main of which is a loss of efficiency and risk for the health

DISCLOSURE OF INVENTION

It was thus object of the present invention to overcome the disadvantages mentioned above and to provide an improved process for obtaining pharmaceutical forms with controlled release of the active ingredient. In particular, it was object of the present invention to provide pharmaceutical forms from which the active ingredient could be released in a delayed or rapid but controlled manner based upon the choice of the excipients, and that could be prepared in a simple way without employing solvents or using a prolonged heating, and that could be used with the most drug presently utilized in both the normal and the controlled release compositions.

This aim could be surprisingly attained by means of mechanical and electromechanical actions with frequency ranging from 1 kHz and 2 MHz applied on a mixture comprising the active ingredient and one or more excipients selected in such a way to obtain a form suitable for the administration routes mentioned above.

The present invention provides accordingly an improved process for preparing pharmaceutical forms for oral, topical or parenteral administration with controlled release of the active ingredient, said form comprising a mixture consisting of selected excipients and one or more active ingredients compatible each other and with said excipients, characterized in that one or more excipients are mixed with one or more active ingredient compatible each other and with said excipients, and the mixture thus obtained is exposed to mechanical or electromechanical actions for a well established time and of frequency between 1 kHz and 2 MHz to give a matrix, a tablet or a mono or multilayered film which is able to release the active ingredient in the stomach, in gut or for contact to the skin or in a body fluid in slow or rapid but controllable manner.

If it is desired, the matrix, tablet or mono or multilayered film can be subjected to crushing according to usual methods to give pellets or granules having a diameter of 2.5 mm at most, which then could be inserted in usual capsules and as such they are pellets or granules able to release the active ingredient therein contained in a delayed or quick but always controlled manner.

Further object of the present invention are also the pharmaceutical forms thus obtained and their use in human or veterinary field for the oral, topical or parenteral administration, or in agroindustrial field for the controlled release of for example pesticides, vegetal hormones, fragrances and the like.

The frequency of the mechanical or electromechanical actions utilized for the practice of the present invention is normally ranging from 1 kHz to 2 MHz.

The mechanical and electromechanical actions are usually applied for a brief period of time, usually for a period of from 1/10 to 20 seconds. Based upon the length of time and frequency, tablets or matrices will be obtained having a diameter of 2–15 mm, or mono or multilayered films with a size of from 4 mm to 30 cm, while in every form the thickness will range of from 0.1 to 10 mm. The thickness will depend on the active drug, the desired release time and on the employed excipient(s). As mentioned above, the tablet, matrix or mono or multilayered film can be eventually subjected to a further size reduction (crushing) to give granules having a diameter of 2.5 mm at most, which are then introduced in hard gelatine capsules or blister and are able to release the active ingredient in slow or rapid manner, while they are more soluble than the usual powders containing the same drugs and do not present dosage limits. The pharmaceutical composition in granulate or powder form has the great advantage that it can be supplied by the manufacturer to every person having in mind to prepare pharmaceutical forms of different type (tablets, capsules, suspensions, etc.).

Further to the introduction in hard gelatine capsule, the powders and granulates are able to be processed to give different compositions well known to a person skilled in the art and they do not weigh heavily upon the final cost.

It is evident that the improvements attained with the aid of pharmaceutical forms object of the present invention are noteworthy. In fact it is not necessary to turn to the usual methodologies such as wet or dry granulation, film-forming and so on for obtaining the desired release of the drug. With the process of the invention it is in fact sufficient only to select the active ingredients (s) and then expose the whole to mechanical or electromechanical actions. With said term, any compression effect is meant, mainly perpendicular to the treatment plane (even though not necessarily), which is able to provide a reduction of the bulk density, a temporary heating, changes or permeations of active ingredients and excipients lattice. Under the mechanical or electromechanical actions term, the processes able to provide energy in frequency are included, such as ultrasonic energy, and all those compression and compaction procedures which could be generated also operating beyond the frequency limits mentioned above. As previously described, the product thus obtained can be eventually crushed and employed in powder or granulated form.

It was surprising to find that, based upon the employed excipient, a delayed or rapid but controlled release of the drug can be attained. Thus, by employing for example well known polymers, a delayed release will be obtained, whereas by selecting another excipient a much more rapid release will be achieved. Illustrative examples of said excipients allowing to have a rapid release are the solid sugars and cyclodextrins. Preferred sugars are for example lactose, fructose, maltose, arabinose and saccharose, and the cyclodextrins are selected from the group consisting of α-cyclodextrin, β-cyclodextrin, Γ-cyclodextrin or derivatives thereof, or a mixture thereof.

Illustrative examples of biologically active substances which can be evenly distributed in the matrix employing the mechanical or electromechanical actions are: vitamins, enzymes, antibiotics (such as tetracyclines, penicillins, cephalosporins), diuretics, sedatives, analgesics, bronchodilators, carotenoids, β-blockers, antinflammatorics, anti-depressives, antidiabetics, lipids, antihypertensives, vasodilators, vasoconstrictors, hormones, steroids, antihistamines, antitussives, alkaloids, amino acids, antipyretics, antibacterial agents, amphetamins, hypnotics, tranquilizers, symphatomimetics, barbiturics, anti-parkinson agents, antimalarials, antispasmodics, several topic ophtalmic drugs and so on. Also interferon, antigens, antibodies, polysaccharides, growth factors, anticancer agents, phytohormones, pesticides, pheromones, fragrances, preservants, etc.

Typical examples of suitable drugs include: dexamethasone, prednisolone, isoproterenol, propranolol, codeine, atropine, hyoscyamine, morphine, streptomycin, cortisone, isosorbide-5-mononitrate, amobarbital, scopolamine, theophylline, ephedrine, urapidil, ketoprofen, paracetamol, indomethacin, diltiazem, diacerhein, phenylpzopanolamine and biliary acids.

The polymers or copolymers useful for preparing the matrix, which can be utilized alone or in any mixture thereof, comprise all those already employed in the controlled release pharmaceutical compositions, for example cellulose and its derivatives, polymides, acrylic polymers, polyesters, polyvinylpyrrolidone, starch, polyethylene glycols, polystyrene, polyvinylalcohol, myristyl alcohol and stearyl alcohol polymers, polyvinyl acetate, polybutadiene, polyvinyl formal, polyvinylbutyral, vinyl chloride-vinyl acetate copolymer, ethylene-vinyl acetate copolymer, vinyl chloride-propylene-vinyl acetate copolymer and any mixture thereof. The present invention is not restricted to the employed polymers or active ingredients.

In order to evaluate the efficiency of the new formulation object of the present invention, tablets having a 6 mm diameter and a thickness of 4 mm, each containing a suitable water soluble substance and a water insoluble drug, have been prepared. First, a test was performed for ascertaining whether any decomposition of the active ingredient occurred: the tablets obtained by exposing the excipient/drug mixture to mechanical or electromechanical action, have been tested for the in vitro release rate in aqueous medium. In all the evaluated cases, active ingredient revealed to be absolutely unchanged. The microscope evaluation allowed moreover to ascertain a homogenous distribution of the drug in the matrix. Furthermore, the crystallographic and thermographic tests have evidenced chemical-physical interactions and reticular compenetration not achievable with other compaction procedures usually employed in pharmaceutical field. Analogous effects have been noticed also in the majority of the other compactates obtained using this procedure.

For further evaluating the efficacy of the new formulations according to the present invention, tablets having a 11 mm diameter e 4 mm thickness were prepared, each tablet containing suitable water soluble excipients and active ingredients with different water solubility. The tablets were then crushed to give pellets having a diameter of from 0.9 to 1.2 mm. First, it was ascertained whether any alteration of active ingredient did occur; to this end, the powder obtained by electro-beating action was examined for the release rate in vivo in aqueous medium. The active ingredient revealed to be fully unchanged in all the tested samples, and this in an extent of 99.5%. The electronic microscope evaluation allowed then to ascertain an "interstitial" distribution of the drug in the matrix (FIG. 5). Comparison with the dirtibution of a drug in a standard tablet is clearly evident (FIG. 6).

It has benn further verified that the release rate can be modified at will by adding a small amount of a substance able to modify hydrophily-lipophily of the composition to the mixture active ingredient/excipient. Said substances can be selected from the group consisting of polyethylene glicol, fatty acids and their salts, talc, paraffins, waxes, hydrogenated fats, gelatin, gum arabic, agar, albumin, gluten and triglycerides. Without being bound to any theory, it is believed that said additive under mechanical or electromechanical action melts and soakes the solid, surrounding matrix, thus modifying strongly the water penetration rate and thus dissolution rate and drug bioavailability.

Logically, the release kinetic can be regulated at will by varying the amount and/or nature of the polymeric materials and/or excipients employed for obtaining the matrix. The relative proportions of the composition to be exposed to mechanical or electromechanical action can be modified over a wide range depending upon the active ingredient to be administered or the desired effect. Generally, the active ingredient can be present in an amount which will be released over controlled periods of time, according to predetermined desired rates, which rates are dependant upon the initial concentration of the active ingredient in the matrix and the level of mechanical or electromechanical action to which it is subjected. Proportions suitable for the purpose of this invention can range from about 30 to 75% by weight of active ingredient and about 70 to 25% by weight of excipient (s) to give 100% by weight of the final system.

It is also clear that any person skilled in the art could modify the present invention utilizing another drug or different substances for having the synthetic matrix. It appears thus to be superfluous to point out as such modifications belong in toto to the invention as described above, and therefore they could not be retained as different from the claims as reported here below.

BRIEF DESCRIPTION OF THE DRAWINGS

To show the efficacy of the employed method, comparisons between the new pharmaceutical forms and those obtained by usual compaction were carried out. The results will be discussed in the following examples and in the accompanying drawings. In said drawings, FIGS. 1–4 are explained in the Examples, whereas

The forms object of the present invention are illustrated in the following Examples. Since the Examples are for illustrative purposes, they should not be construed as limiting. All "%" are by weight unless otherwise specified.

EXAMPLE 1

This example shows the increase of the dissolution rate of the active ingredient contained in a solid oral formulation.

A mixture comprising 68% spray-dried, free flowing lactose (able to be directly compressed), 30% indomethacin (particle diameter: 60% <85 μm; 98% <105 μm), 1% talc and 1% magnesium stearate, was homogenously worked in a Turbula T2C® mixer.

Said mixture was then divided in two portions, one of which was compressed at a compression force of 35,000 N/cm$^2$ by means of an alternative Korsch EKO® apparatus to give tablets having a 11 mm diameter and a weight of 350 mg (tablet A). The other portion was compacted according to the invention (tablet B, frequency 30 kHz, energy 400 J). Strength, measured with a Monsanto apparatus, resulted to be 5 kg for tablet A and 7.5 kg for tablet B.

Both tablets A and B were subjected to the in vitro dissolution test in a laminar flow column dissolver operating at open circuit and employing a buffer solution of pH 7.4 as dissolution medium (flow=12.5 ml/min at 37° C.).

Figure 1:
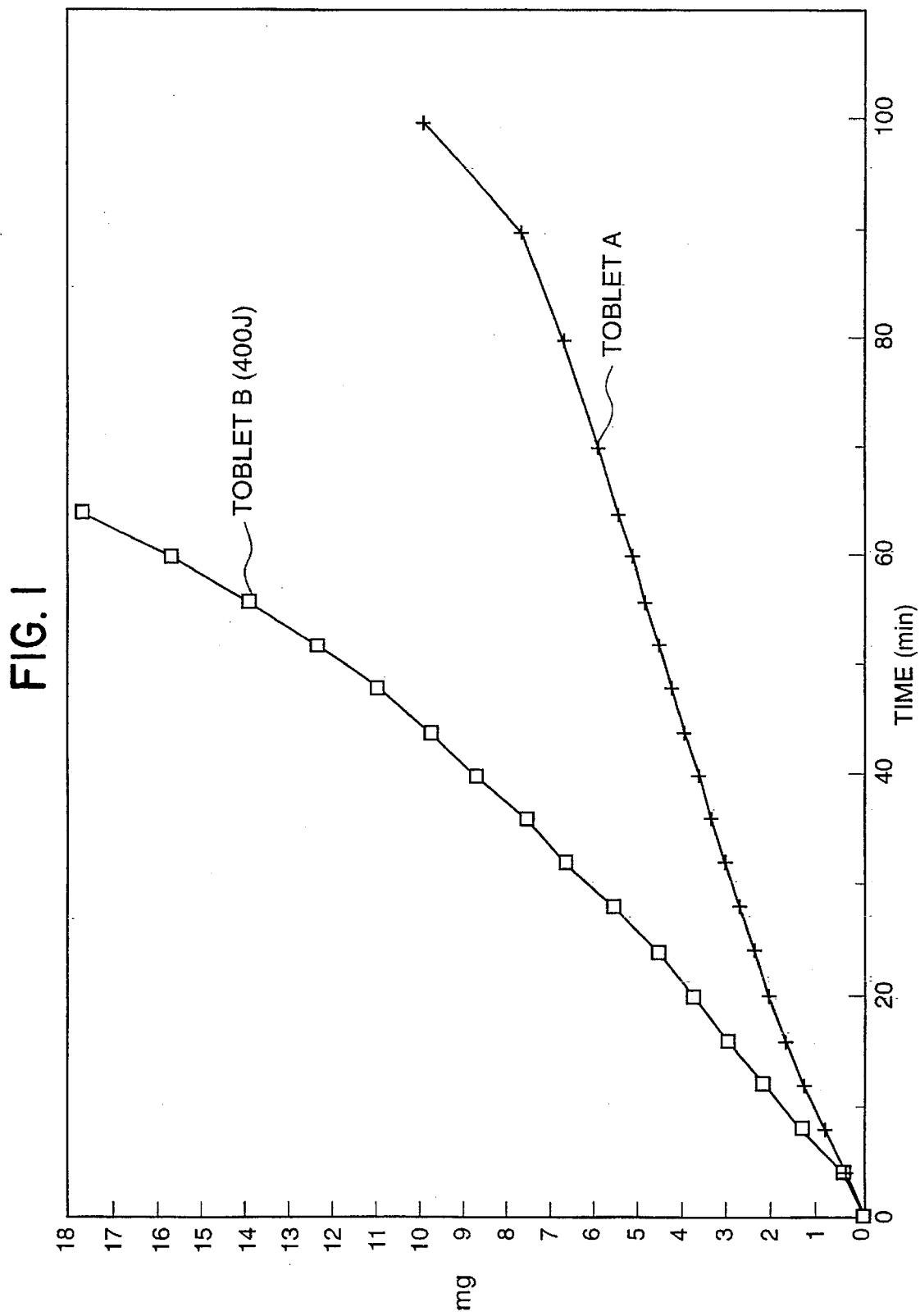

Curves a and b in FIG. 1 show the amount of indomethacin gone in solution (mg) vs time for tablets A and B respectively (each point of said graphs shows the average value obtained in 5 tests). As it is clear from said graph, with the formulation compacted according to the present invention a dissolution rate of more than 100 fold can be obtained (100% quicker).

EXAMPLE 2

In this Example the preparation of a prolonged release granulate is described. A mixture comprising 68% of a directly comprimible Eudragit RPL®, 30% anhydrous theophylline and 1% of both talc and magnesium stearate, after treatment in Turbula T2C mixer, was divided in two equal parts. The first portion was compacted by means of an alternative Korsch EKO apparatus operating at 40,000 N/cm$^2$, to give tablets having a diameter of 11 mm and weighing 400 mg±4.5% (tablet A).

The second portion of the powder was compressed according to the present invention by providing each tablet, weighing 400 mg±3% and having a diameter of 11 mm, with an energy of 400 J (tablet B).

The strength was as stated above in Example 1 (5 kg±2%).

Both tablets A and B were separately transformed in a granulate by means of a dry Erweka TG II S granulator, and both the granulates were then classified in a vibrating screen, keeping the fractions having a diameter of 100 and 150 μm, denominated granulate A and B respectively.

Figure 2:
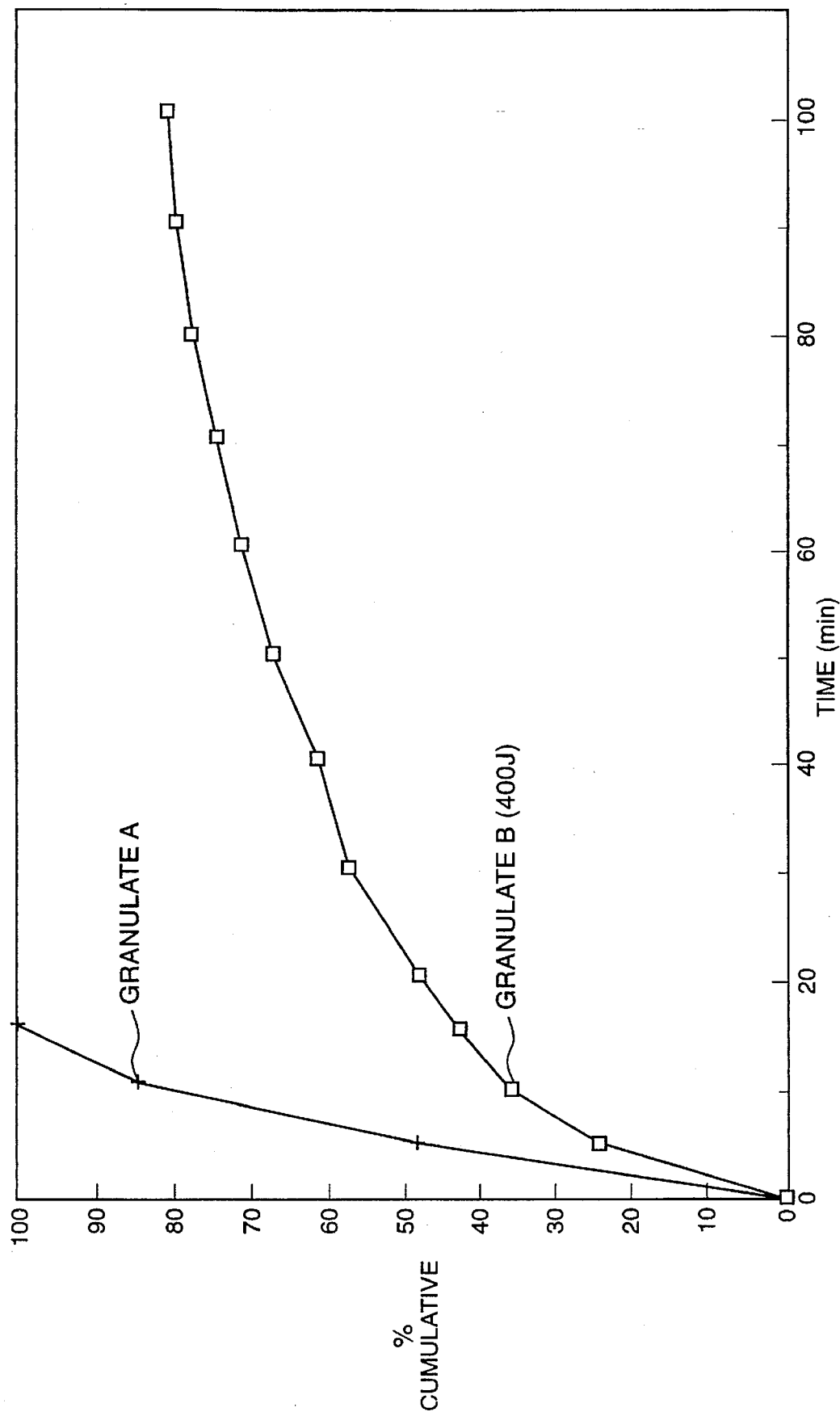

FIG. 2 shows the dissolution curves (cumulative % of released theophylline) for granulate A (a curve) and B (b curve) respectively, as measured in a laminar flow column dissolver operating at open circuit and at 37° C., using a buffer solution of pH 7.4 as dissolution medium (flow=12.5 ml/min).

As evident, the dissolution rate is clearly lower for granulate B and an analogous difference in the dissolution rate can be ascertained for the tablet obtained by compaction of granulate A and B in an alternative apparatus.

EXAMPLE 3

In this Example the preparation of prolonged release monolithic compactates is described. First, a mixture comprising equal amounts of Eudragit RS and Eudragit RLP (both these materials being able to be employed in direct compression) was prepared, and it was made homogenous by treatment in a Turbula T2C mixer for 10 minutes. This composite powder was thereafter referred as powder A.

The following mixtures were then prepared:

30% anhydrous theophylline, 68% powder A, 1% of both talc and magnesium stearate (mixture B);

50% anhydrous theophylline, 48% powder A, 1% of both talc and magnesium stearate (mixture C);

75% anhydrous theophylline, 23% powder A, 1% of both talc and magnesium stearate (mixture D). Each of the mixtures thus obtained was treated in a Turbula T2C mixer and then it was compacted according to the invention subjecting each tablet, having a diameter of 11 mm and weighing 400 mg, to an energy of 400 J (frequency 30 kHz). Tablets Bm, Cm and Dm were thus obtained.

A portion of mixture B was then compacted in an alternative Korsch EKO apparatus operating at 3500 N/cm$^2$ to give tablets of 400 mg and with a diameter of 11 mm (tablets Bk).

Figure 3:
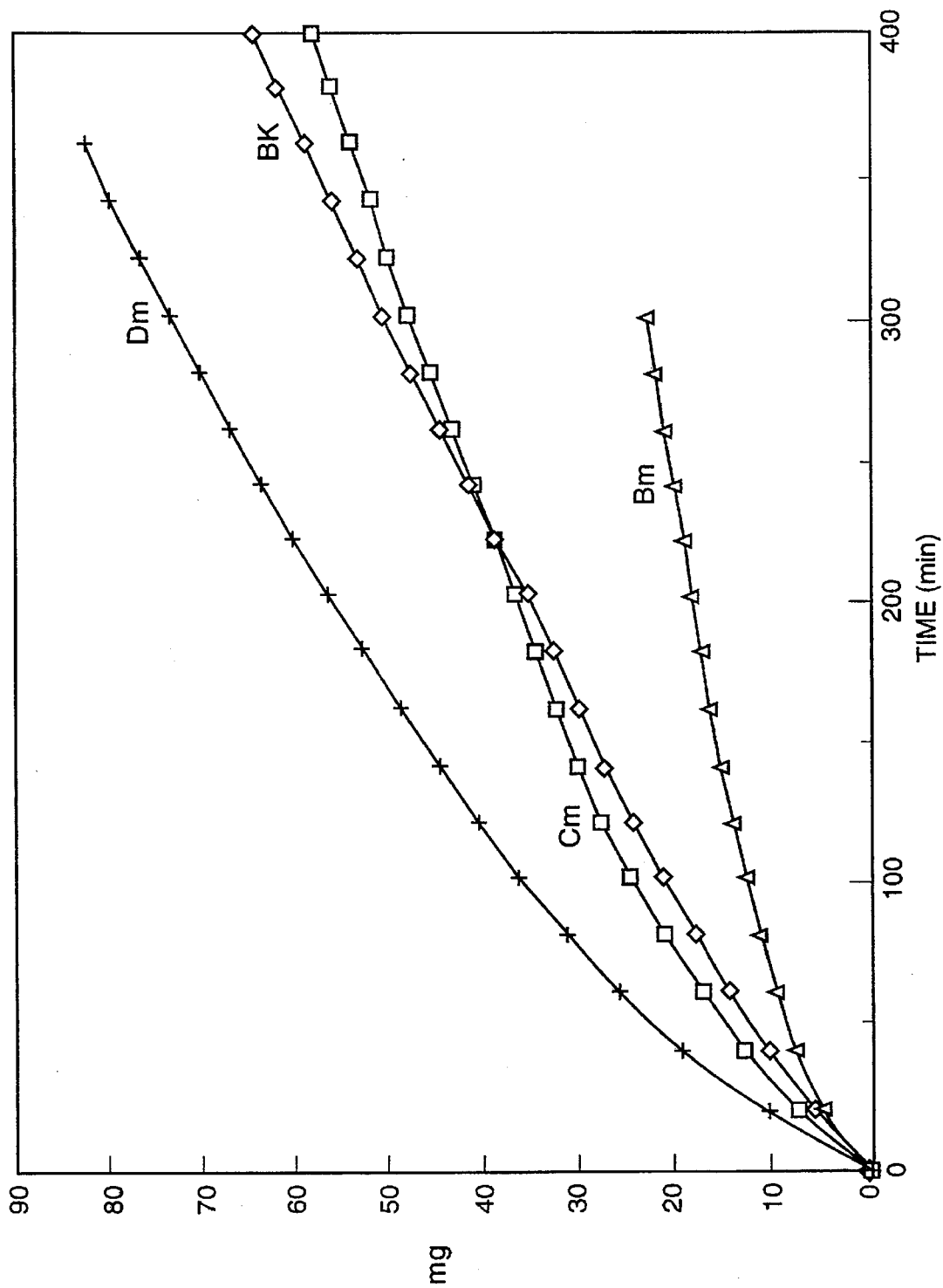
Figure 4:
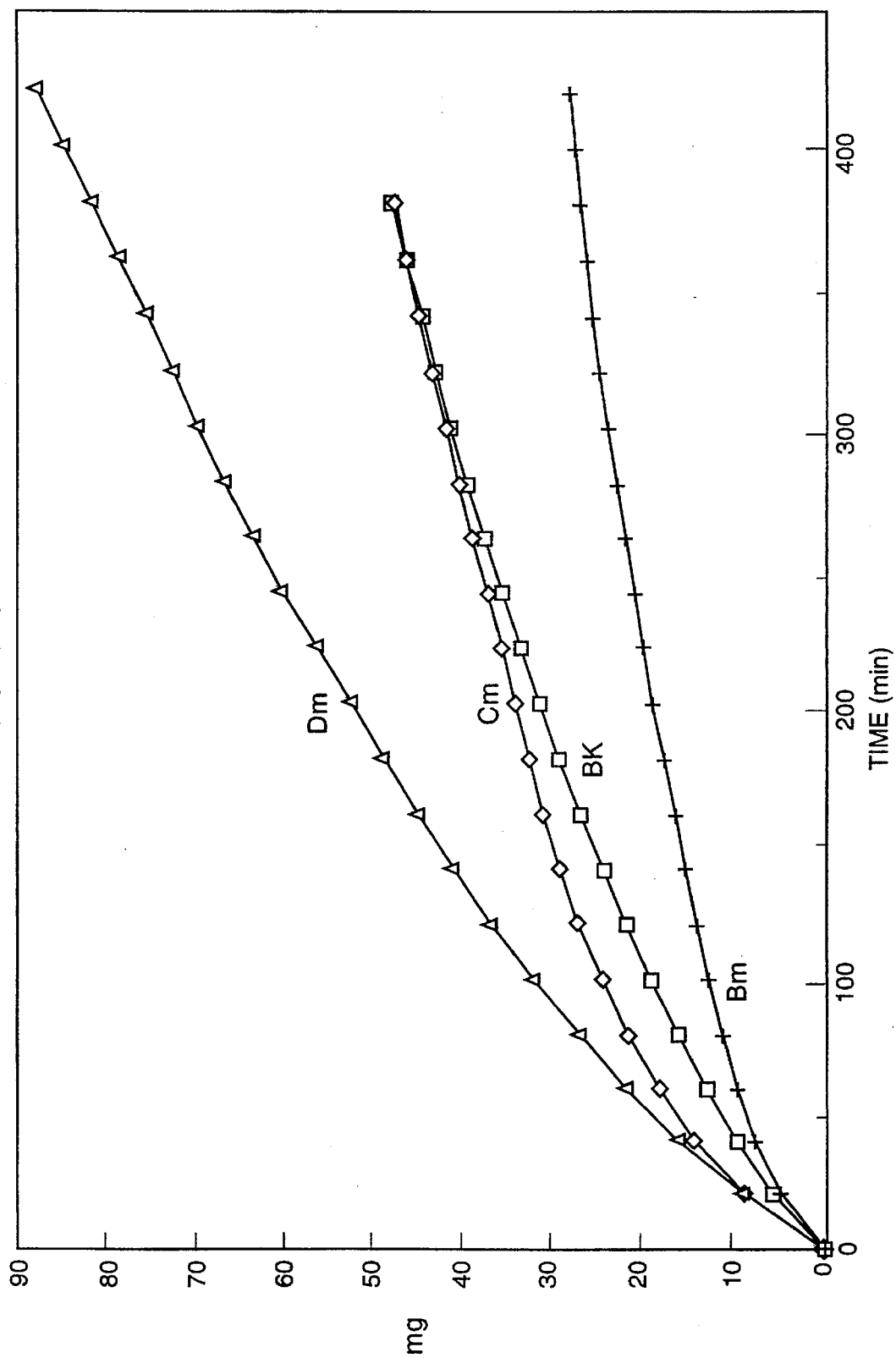
Figure 5:
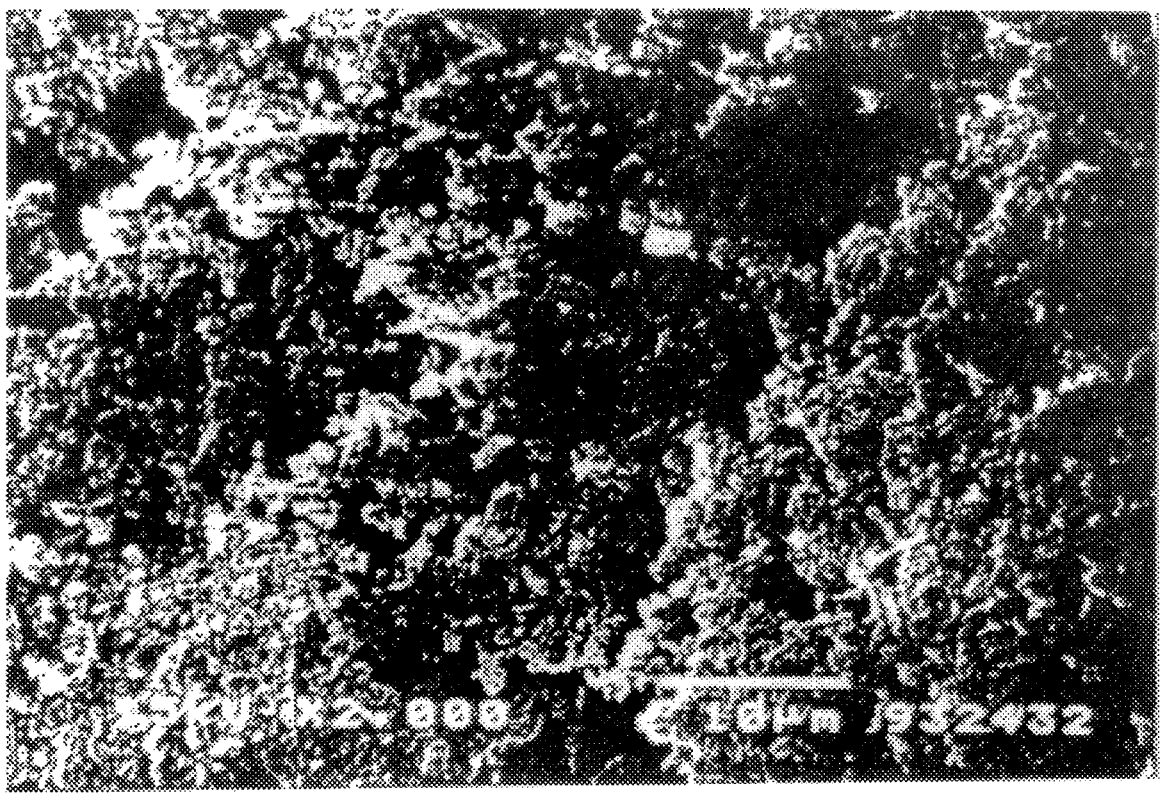
FIG. 5 is a microphotograph of a section of a tablet containing excipients+active ingredient: Korsch apparatus, compression power 5000 kg/cm$^2$.
Figure 6:
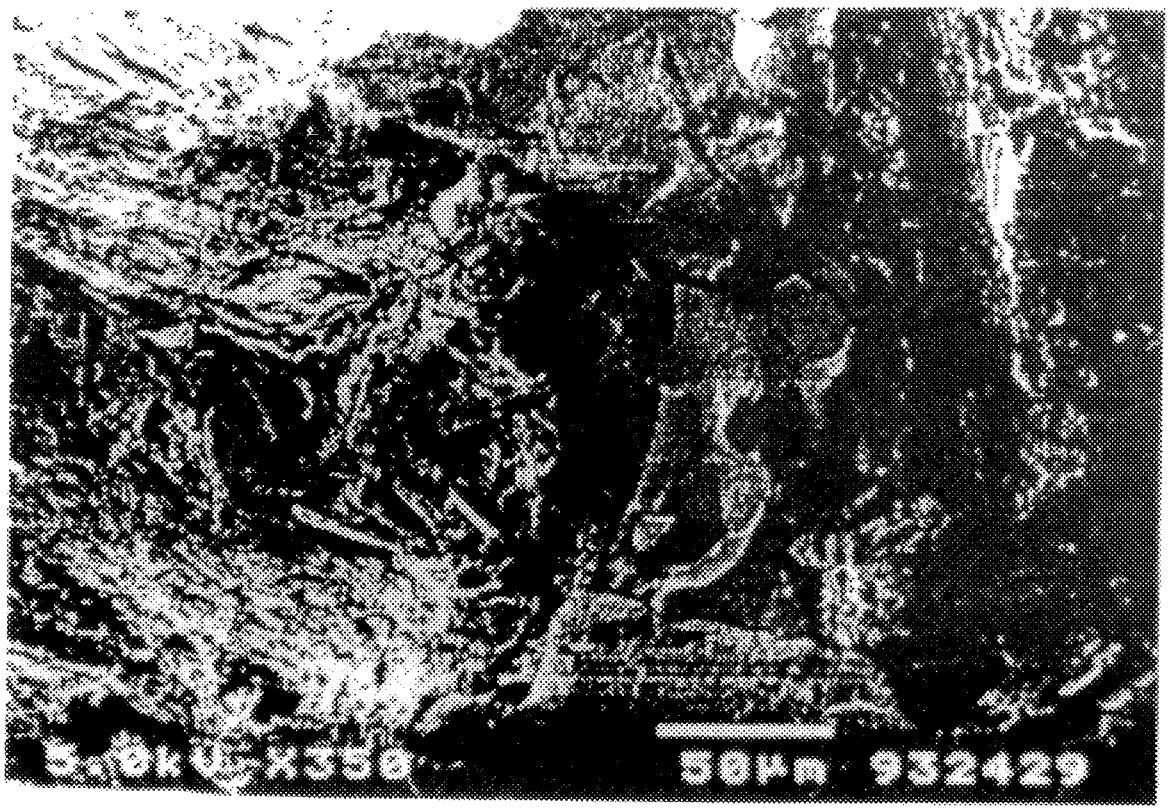
FIG. 6 is a microphotograph of the same composition as in FIG. 5, but subjected to compaction according to the invention.
Figure 1:
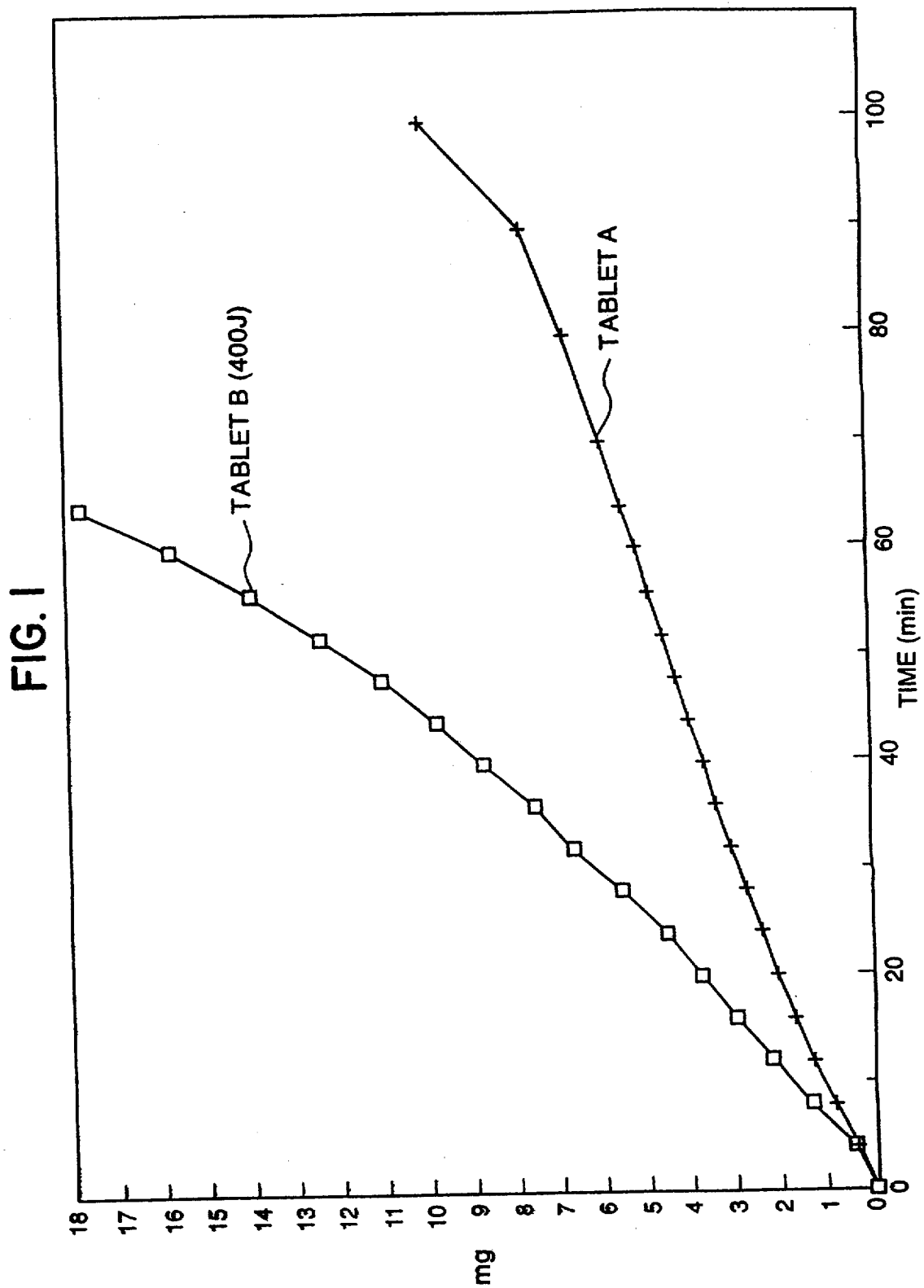

FIGS. 3 and 4 show the dissolution rate vs time (mg of theophylline) for tablets Bm, Cm, Dm and Bk in a laminar flow column dissolver (12.5 ml/min and 37° C.) operating at open circuit at pH 1 (FIG. 5) and pH 7.4 (FIG. 6).

Tablets obtained with the process of the present invention exhibit a clearly lower release rate which is equivalent to the in vitro release of both tablets Cm and Bk, notwithstanding they differs about 100% in the high water soluble theophylline content. The process of the present invention allows moreover to compact easily mixtures with high anhydrous theophylline content, which are unsuitable for a direct compression.

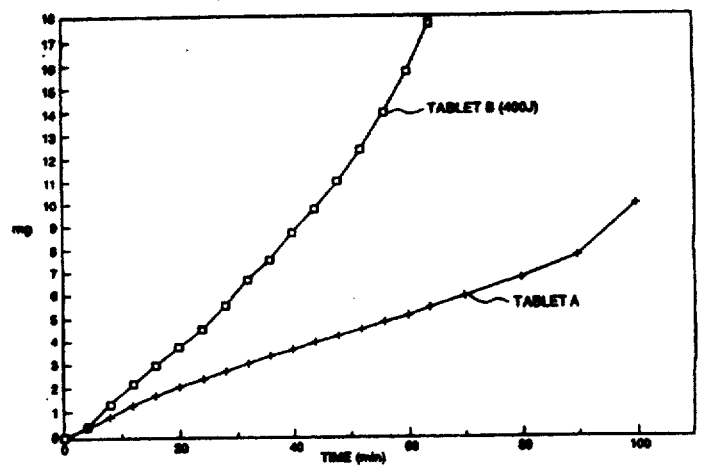

I claim:

1. A process for preparing controlled release pharmaceutical forms, characterized in that a mixture containing from 30 to 75% by weight of an active ingredient and from 70 to 25% by weight of one or more excipients is compacted by means of mechanically or electromechanically generated ultrasonic energy, said ultrasonic energy having a frequency of up to 2 MHz and being emitted for a period of time of from 1/10 to 20 seconds, to give a tablet, matrix, simple or multilayer film, said tablet or matrix having a diameter of from 2 to 15 mm and said film a size of from 4 mm to 30 cm, the thickness being generally of 0.1 to 10 mm.

2. A process according to claim 1, further characterized in that said tablet, matrix or film is then submitted to pelletization to give pellets having a diameter of 2.5 mm at most still maintaining unaltered the ability of a controlled release of the active ingredient.

3. A process according to claim 1, characterized in that the frequency of the mechanically or elctromechanically generated ultrasonic energy is 30 kHz.

4. A process according to claim 1, characterized in that for having delayed release of the active ingredient the excipient is a polymer or copolymer selected from the group consisting of cellulose, polyamide, acrylic polymer, polyester, polyvinylpyrrolidone, polyethylene glycol, polystyrene, polyvinylalcohol, vinyl chloride-vinyl acetate copolymer, ethylene-vinyl acetate copolymer, vinyl chloride-propylene-vinyl acetate copolymer, polyvinylformal, polyvinvylacetate, polybutadiene, polyvinylbutyral and mixtures thereof.

5. A process according to claim 1, characterized in that the excipient is selected from the group consisting of sugars, cyclodextrins and mixtures thereof.

6. A process according to claim 5, characterized in that the sugar is selected from the group consisting of lactose, maltose, saccharose, fructose, arabinose or a mixture thereof.

7. A process according to claim 5, characterized in that cyclodextrins are selected from the group consisting of alpha-cyclodextrin, $\beta$-cyclodextrin, gamma-cyclodextrin, and mixtures thereof.

8. A process according to claim 1, characterized in that for modifying the release rate at will, a substance able to inluence the hydrophily/lipophily of the composition and selected from the group consisting of polyethylene glycol, fatty acid and their salts, talc, gelatin, gum arabic, hydrogenated fats, agar, albumin, gluten and triglycerids is added to the excipient/active ingredient mixture.

9. A process according to claim 1, characterized in that the mixture to be compacted by means of the mechanically or electromechanically generated energy comprises one or more active ingredients compatible with each other.

10. Pharmaceutical form with controlled release of the active ingredient for oral, topical or parenteral administration, said form being a tablet, matrix or mono or multilayered film, characterized in that it is obtained by compacting with the aid of pressure and mechanically or electromechanically generated ultrasonic energy of frequency between 1 kHz and 2 MHz and for a period of time of from 1/10 to 20 seconds a mixture comprising from 30 to 75% by weight of an active ingredient and from 70 to 25% by weight of one or more excipients.

11. Pharmaceutical form according to claim 10, characterized in that is obtained by compacting by means of mechanically or electromechanically generated energy and pressure a mixture comprising the active ingredient and or more excipients compatible with each other, the frequency of said ultrasonic energy being 30 kHz.

12. Pharmaceutical form according to claim 10, characterized in that it has a diameter of from 2 and 15 mm if tablets or matrix and a size of from 4 mm to 30 cm if it is a film, and generally a thickness of from 0.1 to 10 mm.

13. Pharmaceutical form with controlled release of the active ingredient, characterized in that it is a pellet having a particle size of 2.5 mm at most, which can be used as such or inserted in hard gelatine capsules, and is obtained by crushing the tablet, matrix or film prepared compacting by means of pressure and electrically or electromechanically generated energy having a frequency between 1 kHz and 2 MHz, and emitted for a period of time of from 1/10 to 20 seconds, a mixture comprising from 30 to 75% by weight of the active ingredient and from 70 to 25% by weight of one or more excipients compatible with each other.

14. Pharmaceutical form according to claim 10, to be employed also in veterinary field.

15. Pharmaceutical form according to claims 10, to be employed also in agroindustrial field.

16. Pharmaceutical form according to claim 10, characterized in that it contains one or more polymers or copolymers compatible with each other and with the active ingredient, or it contains one or more excipients compatible with each other and with said active ingredient.

17. Pharmaceutical form according to claim 16, characterized in that it contains one or more excipients selected from the group consisting of lactose, fructose, maltose, arabinose, saccharose, $\alpha$-cyclodextrin, $\beta$-cyclodextrin and $\gamma$-cyclodextrin.

18. Pharmaceutical form according to claim 16, characterized in that for delayed release the excipient is selected from the group consisting of cellulose, polyamide, acrylic polymer, polyester, polyvinylpyrrolidone, polyethylene glycol, polystyrene, polyvinyl alcohol, vinyl chloride-vinyl acetate copolymer, ethylene-vinyl acetate copolymer, vinyl chloride-propylene-vinyl acetate copolymer, polyvinyl formal, polyvinylacetate, polybutadiene, polyvinyl butyral, and mixtures thereof.

19. Pharmaceutical form according to claim 10, characterized in that for modifying the release rate at will, a substance able to modify the hydrophily/lipophily of the composition and selected from the group consisting of polyethylene glycol, fatty acids and their salts, talc, gelatin, gum arabic, hydrogenated fats, agar, albumin, gluten and triglycerides is added to the excipient/active ingredient mixture.

20. The pharmaceutical form of claim 13, wherein the electrically or electromechanically generated energy has a frequency of 30 Khz.

* * * * *

UNITED STATES PATENT AND TRADEMARK OFFICE
CERTIFICATE OF CORRECTION

PATENT NO. : 5,662,935
DATED : Sept. 2, 1997
INVENTOR(S) : Motta, Giuseppe

It is certified that error appears in the above-identified patent and that said Letters Patent is hereby corrected as shown below:

The title page, should be deleted to be replaced with the attached title page.

The drawing sheet, consisting of Fig. 1, should be deleted to be replaced with the drawing sheet, consisting of Fig. 1, as shown on the attached page.

Signed and Sealed this

Fourteenth Day of April, 1998

Attest:

BRUCE LEHMAN

Attesting Officer

Commissioner of Patents and Trademarks

United States Patent [19]

Motta

[11] Patent Number: 5,662,935
[45] Date of Patent: Sep. 2, 1997

[54] PROCESS FOR PREPARING CONTROLLED RELEASE PHARMACEUTICAL FORMS AND THE FORMS THUS OBTAINED

[75] Inventor: Giuseppe Motta, Bologna, Italy

[73] Assignee: Saitec S.R.L., Castel Guelfo de Bologna, Italy

[21] Appl. No.: 464,708

[22] PCT Filed: Dec. 23, 1993

[86] PCT No.: PCT/IT93/00136

§ 371 Date: Jun. 23, 1995

§ 102(e) Date: Jun. 23, 1995

[87] PCT Pub. No.: WO94/14421

PCT Pub. Date: Jul. 7, 1994

[30] Foreign Application Priority Data

Dec. 23, 1992 [IT] Italy ............... B092A0455
Jun. 24, 1993 [IT] Italy ............... B093A0294
Nov. 12, 1993 [IT] Italy ............... B093A0460

[51] Int. Cl.$^6$ ............... A61K 9/14; A61K 9/22; A61K 9/24; A61K 9/26; A61K 9/52

[52] U.S. Cl. ............... 424/465; 424/424; 424/425; 424/443; 424/456; 424/457; 424/458; 424/464; 424/468; 424/469; 424/472; 424/484; 424/485; 424/486; 424/487; 424/488; 424/489; 514/770; 514/772.2; 514/772.3; 514/772.6; 514/774; 514/777; 514/781; 514/776; 514/782; 514/784; 514/951; 514/953

[58] Field of Search ............... 424/464, 465, 424/489, 486, 487, 488, 484, 485, 452, 425, 443, 456

[56] References Cited

U.S. PATENT DOCUMENTS 2,828,206  3/1958  Rosenberg ............... 99/2
3,078,216  2/1963  Greif ............... 167/82
3,137,630  6/1964  Hecker et al. ............... 167/81

(List continued on next page.)

FOREIGN PATENT DOCUMENTS 15381    9/1980  European Pat. Off. .
80341    6/1983  European Pat. Off. .
0 123 470  10/1984  European Pat. Off. ..... A61K 31/135
392608   10/1990  European Pat. Off. .
1044572  10/1966  United Kingdom ........... A61K 3/76
92 5774   4/1992  WIPO .

OTHER PUBLICATIONS

Patent Abstract of Japan, JP 3287544, Dec. 18, 1991, vol. 16, No., 114, Mar. 23, 1992, see abstract.
DATABASE WPI, Section Ch, Week 7243, Derwent Publications Ltd., Class A03, AN 72–69291T & JP.A.47 020 327 Mar. 4, 1971.
DATABASE WPI, Section Ch, Week 8346, Derwent Publications Ltd., Class B04, An 83–818128 & JP.A.58 172 311 Apr. 2, 1982.
DATABASE WPI, Section Ch, Week 8908, Derwent Publications Ltd., Class A03, AN 89–057693 & JP.A.1 009 932 Jul. 1, 1987.
DATABASE WPI, Section Ch, Week 88527, Derwent Publications Ltd., Class A03, AN 85–162944 & JP.A.60 094 403 Oct. 27, 1983.

Primary Examiner—Thurman K. Page
Assistant Examiner—James M. Spear
Attorney, Agent, or Firm—Cushman Darby & Cushman Intellectual Property Group of Pillsbury Madison & Sutro LLP

[57] ABSTRACT

An improved process for preparing controlled release pharmaceutical forms comprises exposing a mixture comprising one or more excipients and one or more active ingredients compatible with each other and with said excipients to mechanical or electromechanical actions for a well established time and within a wide range of frequencies to give tablets, matrices or mono or multilayered films. Said forms can be optionally crushed to give a granulate or powder. Depending on the employed excipient, a delayed or rapid but always controllable release of the active ingredient can be attained.

20 Claims, 6 Drawing Sheets